US005917038A

United States Patent [19]
Hay et al.

[11] Patent Number: 5,917,038
[45] Date of Patent: Jun. 29, 1999

[54] PROCESS OF PREPARING SUBSTITUTED ACRYLAMIDES

[75] Inventors: Lynne Ann Hay; David Mitchell, both of Indianapolis, Ind.

[73] Assignee: Eli Lilly and Company, Indianapolis, Ind.

[21] Appl. No.: 08/838,635

[22] Filed: Apr. 11, 1997

Related U.S. Application Data

[60] Provisional application No. 60/031,673, Nov. 22, 1996.
[51] Int. Cl.$^6$ ...................... C07D 265/30; C07D 235/54; C07C 233/00; C07C 235/00; C07C 237/00; C07C 239/00
[52] U.S. Cl. .................. 544/176; 548/307.1; 548/338.1; 548/479; 548/530; 548/550; 549/77; 560/250; 564/182; 564/204
[58] Field of Search ...................................... 564/182, 204; 548/307.1, 338.1, 479, 530, 550; 549/77; 544/176; 560/250

[56] References Cited

U.S. PATENT DOCUMENTS

| | | | |
|---|---|---|---|
| 3,499,928 | 3/1970 | Peterson | 260/570.5 |
| 3,657,340 | 4/1972 | Johnson et al. | 260/557 |
| 3,657,342 | 4/1972 | Peterson | 260/558 |
| 3,657,343 | 4/1972 | Peterson | 260/558 |
| 3,822,313 | 7/1974 | Norell | 260/561 R |
| 5,334,750 | 8/1994 | Kaufmann et al. | 560/104 |
| 5,573,999 | 11/1996 | Sauter et al. | 504/266 |

OTHER PUBLICATIONS

A. Arcadi, et al. "Palladium–Catalysed Reductive Addition of Aryl Iodides to Aryl and Alklethynylsilanes: A Stereo and Regioselective Route to Functionalized 2,2–Disubstituted Vinylsilanes" *Tetrahedron Letters* 27(52):6397–6400 (1986).

S. Cacchi. "The Palladium–Catalyzed Reaction of Aryl Iodides with Mono and Disubstituted Acetylenes: A New Synthesis of Trisubstituted Alkenes" *Tetrahedron Letters* 25(29):3137–3140 (1984).

S. Casson and P. Kocienski. "The hydrometallation, carbometallation, and metallometallation of heteroalkynes" *Contemporary Organic Synthesis* 19–34.

F. Ishikawa. "Cyclic Guanidines. X.[1)] Synthesis of 2–(2,2–Disubstituted Ethenyl–and Ethyl)–2–imidazolines as Potent Hypoglycemics[2)]" *Chem. Pharm. Bull.* 28(5):1394–1402 (1980).

W. Truce and G. Tichenor. "Effect of Activating Group on Trans Steroselectivity of Thiolate Additions to Activated Acetylenes" *J. Org. Chem.* 37(15):2391–2395 (1972).

*Primary Examiner*—Floyd D. Higel
*Attorney, Agent, or Firm*—Janelle D. Strode

[57] ABSTRACT

The present invention relates to a process for preparing acrylamides; wherein, a propiolamide is reacted with an activated aromatic ring to yield a wide variety of acrylamides.

8 Claims, No Drawings

PROCESS OF PREPARING SUBSTITUTED ACRYLAMIDES

This application claims the benefit of U.S. provisional application Ser. No. 60/031,673 filed Nov. 22, 1996.

FIELD OF INVENTION

The present invention relates to the field of organic chemistry. More specifically, the present invention provides synthetic methodology useful in the reparation of functionalized acrylamides.

BACKGROUND OF THE INVENTION

Acrylamides, while often containing biological activity themselves, also provide a valuable framework for the synthetic organic chemist. The construction of sophisticated trisubstituted olefins is a desire of many chemists. Despite the fact that acrylamides are known in the art, the methodology for construction of these systems is limited. In addition, there few syntheses of acrylamides which are both efficient and regioselective. For example, in the case of palladium catalyzed hydroarylation reactions, the addition of the aromatic group can occur at either carbon atom of the alkyne resulting in two different regioisomers. Typically, the addition occurs at each carbon atom of the alkyne with equal frequency. As a result the product of the reaction is a 1:1 mixture of regioisomers. Subsequently, controlling the regioselectivity of this reaction has been a problem consistently recognized in the art. In an attempt to control regioselectivity, artisans have attempted and achieved some level of regiochemical control by varying the steric environment of the alkyne and by combining steric influences with palladiumhydroxyl coordination. No methodology has been identified to date, however, that satisfactorily controls the regioselectivity of hydroarylation reactions of a variety substrates. Most importantly, this type of hydroarylation reaction has never been employed on a propiolamide substrate.

SUMMARY OF INVENTION

The present methodology represents a pioneering invention related to the preparation of functionalized acrylamides by providing a novel method of preparing substituted acrylamides through the reaction of a propiolamide and an activated aromatic ring under hydroarylation conditions. This methodology has the advantage of expanding the realm of starting materials that the chemical practitioner may utilize to prepare acrylamides. This access to varied starting materials then allows preparation of new and more sophisticated acrylamides. In addition, the present invention unexpectedly and surprisingly found that when a propiolamide is subjected to hydroarylation conditions, the resulting products can also be formed in a highly regioselective manner, wherein the aromatic group adds to the carbon of the propiolamide β to the amide, resulting in a trans configuration.

Acrylamides capable of being prepared include numerous biologically active molecular motifs. The anti-viral benzimidazoles, which are one of the motifs capable of being prepared according to the chemistry disclosed herein, are taught by U.S. Pat. Nos. 4,008,243; 4,018,790; 4,118,573; 4,118,742; and 4,174,454. In addition, the anti-fungal 3,3-diarylacrylic acid amides of Curtze et. al., U.S. Pat. No. 4,910,200; and the compounds of U.S. Pat. No. 4,342,781, can be prepared according the processes disclosed herein.

The present invention provides a process for preparing acrylamides which comprises reacting a propiolamide with an activated aromatic ring system under hydroarylation conditions.

The present invention also provides a process for preparing a compound of Formula (I);

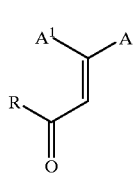

(I)

wherein:

A is aryl, heterocylyl, said aryl or said heterocyclyl is either unsubstituted or substituted;

$A^1$ is aryl or substituted aryl; and

R is a primary or secondary amine;

wherein said process comprises reacting a compound of Formula (II)

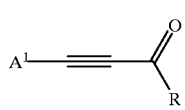

(II)

wherein $A^1$ and R are as defined above; with a compound of Formula (III)

(III)

wherein A is as defined above and X is a leaving group, under hydroarylation conditions.

Accordingly, the present invention also provides for a process of controlling the regioselectivity of a hydroarylation reaction, such that the resulting product has the amide and introduced aromatic ring in a 1,2-trans relationship, by employing a propiolamide as the alkyne substrate in the reaction.

In addition, the invention provides a process of inducing regioselectivity in the coupling of a propiolamide and an activated aromatic ring system such that the resulting product has the amide and introduced aromatic ring in a 1,2-trans relationship.

The present invention provides a process of inducing the regioselective and stereoselective addition of an activated aromatic ring system to a propiolamide such that the resulting product has the amide and introduced aromatic ring in a 1,2-trans relationship.

DETAILED DESCRIPTION OF THE INVENTION

For the purposes of the present invention, as disclosed and claimed herein, the following terms are defined below. As they relate to the present invention, the terms below may not be interpreted, individually or collectively, to describe chemical structures that are unstable or not possible to construct.

The term $A^1$, as used herein, represents hydrogen or an aryl group which is either substituted or unsubstituted.

The term "acrylamide" as used herein represents organic compounds containing the core features depicted below.

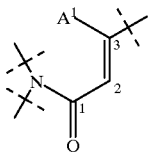

The described acrylamide will be functionalized at the 3 position as depicted. The methodology provided by the present invention is not dependent upon the type or extent of functionalization of the acrylamide. For that reason, primary, secondary, or tertiary amides can be prepared by the methodology disclosed herein; in addition, amides can be cyclic or acyclic. The type or extent of functionalization of the amide is not crucial to the invention.

The term "propiolamide" as used herein represents organic compounds with the core features depicted below.

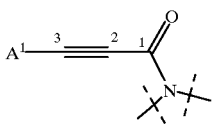

As the skilled artisan will appreciate from the examples disclosed herein, the methodology provided by the present invention is not dependent upon the type or extent of functionalization of the propiolamide. Accordingly, the amide of the propiolamide can be primary, secondary, or tertiary. Since the present invention is not affected by the type or extent of functionalization of the amide, a skilled artisan would appreciate that the present invention would be applicable to a tremendously wide variety of functionalized amides.

The term "activated aromatic ring system", abbreviated Ar-X, wherein X is a leaving group, as used herein, represents any aromatic ring that can oxidatively add to a palladium catalyst. Generally such ring systems are functionalized with a leaving group. The ring system can be monocyclic, polycyclic, partially aromatic or fully aromatic and can contain heteroatoms selected from the group consisting of oxygen, sulfur, or nitrogen. In addition, the ring system may be functionalized or substituted at any position that affords a stable structure.

The term "halo" represents fluorine, chlorine, bromine, or iodine.

The terms "$R^2$ and $R^3$" represent hydrogen, $C_1$–$C_6$ alkyl, or phenyl.

The term "$C_1$–$C_6$ alkyl" represents a straight or branched alkyl group containing from one to sixteen carbon atoms.

The term "$C_1$–$C_6$ alkyl" represents a cyclo, straight or branched chain alkyl group having from one to four carbon atoms such as methyl, ethyl, n-propyl, isopropyl, cyclopropyl, n-butyl, isobutyl, sec-butyl, t-butyl and the like. A "haloalkyl" is one such alkyl substituted with one or more halo atoms, preferably from one to three halo atoms. An example of a haloalkyl is trifluoromethyl. An "alkoxy" is a alkyl group covalently bonded by an —O— linkage. The term "$C_1$–$C_4$ alkyl" is included within the definition of $C_1$–$C_6$ alkyl.

The term "acyl" as used herein, alone or in combination, is derived from an alkanoic acid containing from one to seven carbon atoms. The term "acyl" also includes moieties derived from an aryl carboxylic acid.

The term "aryl" represents a monocyclic, bicyclic, or tricyclic ring system, comprised of carbon atoms, that is either completely or partially aromatic and has a total molecular weight of less than about 600 grams/mole. Representative aryl groups include, but are not intended to be limited to; phenyl, naphthyl, tetrahydronaphthyl, indanyl, fluorenyl, anthracenyl, phenanthracenyl, and the like.

The term "substituted" as used herein means an optional substitution of from one to five, preferably one or two, groups independently selected from halo, $C_1$–$C_6$ haloalkyl, hydroxy, carboxy, tetrazolyl, acyl, $COOR^2$, $CONR^2R^3$, $CONH(C_1$–$C_6$ alkoxy), cyano, $C_1$–$C_6$ alkoxy, $C_1$–$C_6$ alkyl, phenyl, pyrollyl, pyridyl, benzyl, nitro, $NR^2R^3$, $NHCOR^2$, $NHCO$(benzyl), $SR^2$, $OCO(C_1$–$C_6$ alkyl), $SO_2(NR^2R^3)$, or $SO_2R^2$; provided that such substitution does not completely interfere with the hydroarylation reaction described herein.

The term "heterocycle" represents a stable, monocyclic, bicyclic, or tricyclic ring system, having a total molecular weight of less than about 600 grams/mole, that is either completely or partially aromatic and has one or more, preferably one to six, heteroatoms that are the same or different and that are selected from the group consisting of sulfur, oxygen, and nitrogen. The heterocycle may be unsubstituted or substituted at any carbon or nitrogen which affords a stable structure. Examples of a heterocycle include, but are not intended to be limited to; pyrazole, imidazole, isoxazole, oxazole, thiazole, pyridine, pyrimidine, pyrazine, furan, thiophene, benzofuran, indole, benzothiophene, indazole, dibenzothiaphene, benzoxazole, norharman, carbazole, benzimidazole, imidazopyridine, pyridoimidazole, quinoline, isoquinoline, benzoquinoline, quinoxaline, and the like.

The term "leaving group" as used in the specification is well known in the art. Generally, a leaving group is any group or atom that enhances the electrophilicity of the atom to which it is attached for displacement. Representative leaving groups include, but are not intended to be limited to; p-nitrobenzene sulfonate, triflate, mesylate, tosylate, imidate, fluoride, chloride, bromide, iodide, and the like.

The term "hydroarylation conditions" as used herein is well known in the art. Hydroarylation conditions include, but are not intended to be limited to, reacting the substrates in the presence of a palladium catalyst, a base, and a proton source in an appropriate reaction media.

The term "palladium catalyst" as used herein is understood by those skilled in the art to include palladium complexes capable of catalyzing hydroarylation reactions and includes both palladium(0) and palladium(II) catalysts. Representative palladium catalysts include, but are not intended to be limited to; bis(acetonitrile)palladium(II) chloride, palladium(II) chloride, palladium(II) acetate, bis(triphenylphosphine)palladium(II) acetate, bis(triphenylphosphine)palladium(II) chloride, is(benzonitrile)palladium(II) chloride, is(dibenzylideneacetone)palladium(0), palladium(II) trifluoroacetate, tetrakis(triphenylphosphine)palladium(0), and the like.

The term "base" as used herein is well known in the art and includes entities that are employed for the purpose of abstracting or coordinating a proton and is intended to encompass both amine bases and non-amine bases.

The term "amine base" as used herein represents any primary, secondary, or tertiary amine that one skilled in the art would employ for the purpose of abstracting or coordinating to a proton. Suitable amine bases include, but are not intended to be limited to; methylamine, dimethylamine, diethylamine, diisopropylamine, ethyldiisopropylamine, triethylamine, piperidine, pyridine, dimethylaminopyridine, and the like.

The term "primary or secondary amine" is understood by one skilled in the art, upon reading the examples included herein, to encompass amines that would be amenable to the claimed processes. Suitable amines include, but are in no way intended to be limited to: alkylamines such as; methylamine, ethylamine, propylamine, diethylamine, isopropylamine, dimethylamine, butylamine, pentylamine, cyclopentylamine, cyclopropylamine, dicyclohexylamine, cyclohexylamine, hexylamine, heptylamine, octylamine, nonaylamine, diisopropylamine, methylethylamine, ethyldiisopropylamine, and the like; aryl amines such as; aniline, substitututed anilines, anisole, aminophenol, methylmercaptoaniline, N-methlyaminophenol, haloaniline, 1-amino-5,6,7,8-tetrahydrohaphthalene, 4-cylcohexylaniline, N-phenyl-1,2-phenylenediamine, aminobiphenyl, diphenylamine, aminonaphthalene, aminofluorene, substituted aminonaphthalene, benzylamine, substituted benzylamine, substituted phenethylamine, and the like; cyclic amines such as; pyrrole, piperidine, morpholine, tetrahydrofurylamine, 2-methylaminomethyl-1,3-dioxolane, pyrrolidine, substituted pyrrolidine, aminosugars, 2,6-dimethylmorpholine, tetrahydropyrimidine, homopiperazine, perhydroindole, decahydroquinoline, pyridylethylamine, pyridylpropylamine, and the like; carboxyprotected or unprotected D, L, or racemic aminoacids such as; methylphenylglycinate, asparagine, aspartic acid, glutamine, glutamic acid, leucine, glycine, isoleucine, methionine, tyrosine, tryptophan, proline, valine, phenylalanine, and the like; or substituted amino acids such as hydroxyphenylglycine, and the like. In addition, the amine portion of the propiolamide could be functionalized as a carbamate, urea, or imide. As is evident from the examples, a wide variety of propiolamides can be used in the process described herein and a skilled artisan would be able to ascertain the intending meaning of this term by reference to the the teachings included herein in combination with the current skill in the art without undo experimentation.

One method of forming trisubstituted olefins regioselectively and stereoselectively involves the palladium-catalyzed hydroarylation of an alkyne with an aryl iodide. As shown in Scheme 1, this reaction occurs in a stereospecific syn manner, adding the aryl group and a hydrogen atom across the triple bond. See for example, Hudrlik and Hudrlik, *The Chemistry of the Carbon-Carbon Triple Bond. Part* 1 (Ed. Saul Patai), John Wiley, New York, 1978, p. 199–273.

Scheme 1

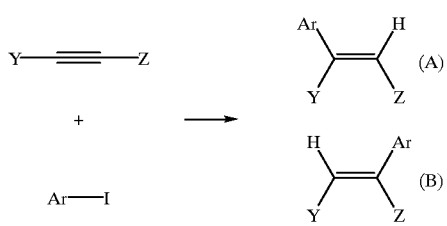

The reaction can proceed via two possible regiochemical pathways resulting in a mixture of regioisomers A and B. The hydroarylation employs palladium catalysis and requires a dialkyl or trialkyl ammonium formate salt to regenerate the active palladium(0) species. Alternatively, other reagents such as alkylsilanes may be used in combination with an acid to regenerate the active palladium(0) species. The mechanism (Scheme 2) is generally believed to involve oxidative addition of the palladium species into the aryl iodide bond (I) Coordination of the Ar-Pd-I complex with the alkyne then occurs (II), followed by a ligand exchange on the palladium with a formate ion (III), and the subsequent decarboxylation to generate the hydride (IV). Reductive elimination of the palladium occurs to give the olefinic product and regenerate the active palladium species (V). See Cacchi et al, *Pure and Aipl. Chem.*, Vol 62, pp. 713–22, 1990.

Scheme 2

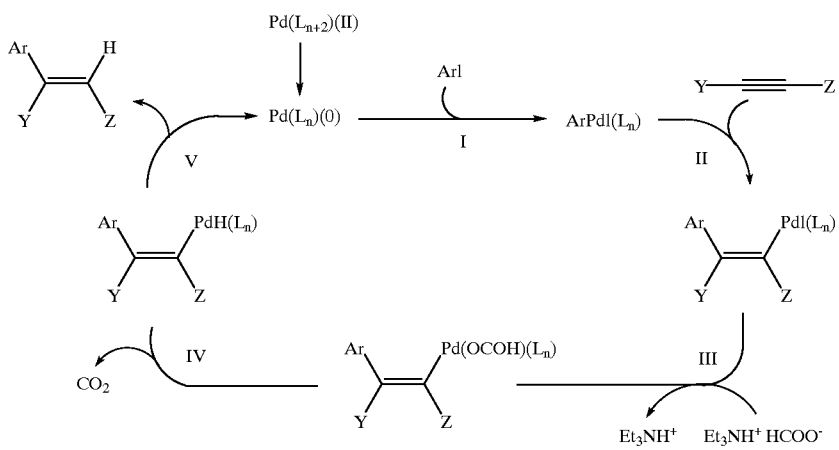

Although this reaction gives very high yields of trisubstituted olefins with symmetrically substituted alkynes (Scheme 1, Y=Z), asymmetrically substituted alkynes can result in poor regioselectivity. To control this regioselectivity, steric effects can be employed. For example, a trimethylsilyl group on one of the acetylenic carbons can direct the hydroarylation through steric bulk, since the aryl group prefers the least hindered site. For example, some regioselectivity has been reported by Arcadi, et al, *Tet. Lett.*, Vol 27, pp. 6370–6400, 1986; where a trimethylsilylalkyne was utilized as a substrate. (Scheme 1, X=SiMe$_3$). See also, Arcadi et al, *Tetrahedron*, Vol 41, pp. 5121–31, 1985.

Another method for controlling the regiochemical outcome is through coordination of a group on one end of the acetylene to the palladium complex. For example, an arylethynyl, dialkyl carbinol not only provides regiocontrol through steric hindrance, but also allows for palladium-hydroxyl coordination. See for example, Arcadi et al, *Tetrahedron*, Vol 41, pp. 5121–31, 1985.

The present invention discloses methodology for controlling the regiochemistry of the hydroarylation reaction described in Scheme I through the use of propiolamide as substrates in the reaction. When propiolamides are utilized as substrates under certain reaction conditions, the resulting products are produced such that the β-regioisomer predominates over the α-regioisomer. The use of a propiolamide in this manner is not described by the art. Therefore, the present invention provides a novel solution to the problem of controlling the regioselectivity of the reaction described in Scheme 3 below.

Scheme 3

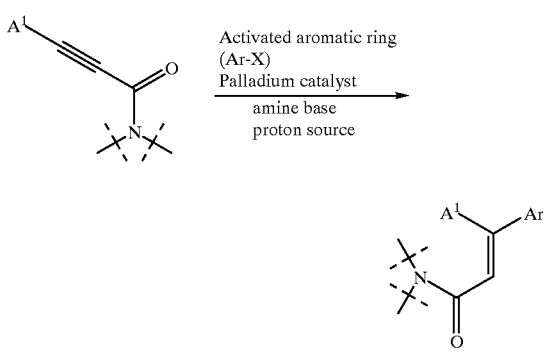

The pioneering aspects of the present invention allow the chemical practitioner to construct highly functionalized acrylamides in a new and efficient manner that is usually accompanied by some degree of regioselective and stereoselective control. The activated aromatic system is introduced into the product at the carbon β to the amide and also in a predominately trans fashion. It is believed that this regiochemical control is the result of the amide functionality of the propiolamide.

The selectivity of the reaction described in Scheme 3 is believed to be the result of a preferred transition state wherein the non-bonding electrons of the amide can participate in the alkyne's binding to the palladium catalyst. As depicted below, the lone pair electrons on either the amide oxygen or nitrogen may contribute to the alkyne's to ability bind to the palladium in a regiospecific manner.

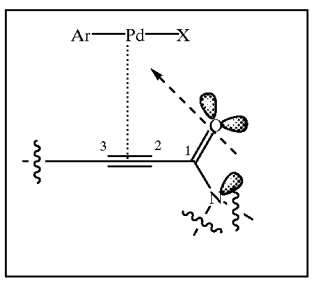

Regardless of whether the oxygen or nitrogen of the amide, or both, is responsible for regiospecific binding to the palladium, the presence of the amide functionality in the substrate molecule is essential for selectivity to be seen in the reaction. In addition, it is clear from the diagram above that the invention resides not with the functionality on the amide or alkyne, but with the presence of the amide itself.

The functionalization of the propiolamide does not interact with the mechanism of the reaction and therefore the reaction described in Scheme 3 is amenable to a surprisingly wide variety of substrates. For example, Ar-X can be any aromatic structure that can oxidatively add to a palladium catalyst. In addition, the propiolamide could be functionalized in any manner and the amide could be any primary, secondary, or tertiary amide including amides wherein the amide nitrogen is one of the atoms of a ring.

Preferred propiolamides are those of a total molecular weight of less than about 1500 grams/mole. More preferred propiolamides are those wherein the 3 position is functionalized with an aryl or substituted aryl. Other preferred propiolamides are those where the 3 position is functionalized with naphthalene, anthracene, phenyl, or phenanthracene; said naphthalene, anthracene, phenyl, or phenanthracene can either be substituted or unsubstituted. More preferred propiolamide are those where the 3 position is functionalized with naphthalene, anthracene, phenyl, or phenanthracene; said naphthalene, anthracene, phenyl, or phenanthracene being either unsubstituted or substituted with from one to five, preferably one or two, groups independently selected from halo, $C_1$–$C_6$ alkyl, $C_1$–$C_6$ haloalkyl, hydroxy, carboxy, acyl, $COOR^2$, $CONR^2R^3$, $CONH(C_1$–$C_6$ alkoxy), cyano, $C_1$–$C_6$ alkoxy, nitro, $NR^2R^3$, $NHCOR^2$, $SR^2$, $SO_2(NR^2R^3)$, or $SO_2R^2$. Most preferred propiolamides are those wherein the 3 position is functionalized with 4-chlorophenyl, 3,4-dimethoxyphenyl, difluorophenyl, or fluorophenyl.

Preferred amide portions of the propiolamide are those wherein the amine portion is prepared from: a $C_1$–$C_{16}$ alkylamine, ammonia, substituted or unsubstituted phenylamine, $C_1$–$C_6$ alkylamine, phenyl $C_1$–$C_6$ alkylamine, substituted phenyl $C_1$–$C_6$ alkyl amine, heterocyclyl $C_1$–$C_6$ alkylamine, substituted heterocyclyl $C_1$–$C_6$ alkyl amine, morpholine, pyrolidine, piperidine, or a protected or unprotected aminoacid. Other preferred amides are those wherein: $R^1$ and $R^{1A}$ are independently at each occurance; hydrogen, $C_1$–$C_6$ alkyl, substituted $C_1$–$C_6$ alkyl, $C_1$–$C_6$ alkoxy, $(CH_2)_n$ aryl, $(CH_2)_n$ substituted aryl, $(CH_2)_n$ heterocyclyl, $(CH_2)_n$ substituted heterocyclyl, $CONR^4R^5$, $CHR^5CO_2R^4$, or $R^1$ and $R^{1A}$ combine, with the nitrogen atom to which they are attached, to form morpholinyl, piperidinyl, pyrrolidinyl, or piperazinyl; and $R^4$ and $R^5$ are independently hydrogen, $C_1$–$C_6$ alkyl, substituted $C_1$–$C_6$ alkyl, $C_1$–$C_6$ alkoxy, $(CH_2)_n$ aryl, or $(CH_2)_n$ substituted aryl; and n is 0, 1, 2, or 3.

Especially preferred amide portions of the propiolamide are those wherein the amine portion is prepared from: morpholine, dimethylamine, methylamine, and ammonia.

The activated aromatic ring can be any aromatic structure that could oxidatively add to a palladium catalyst. Preferred aromatic ring systems are those of a total molecular weight of less than about 1000 grams/mole. More preferred aromatic ring systems include, but are not intended to be limited to; aryl, substituted aryl, heterocycle, substituted heterocycle, and the like. Additional preferred activated aromatic groups include, but are not intended to be limited to; phenyl, pyridyl, benzimidazolyl, naphthyl, benzofuranyl, pyrazole, thiophene, furanyl, benzothiophene, indolyl, and the like, wherein said groups are either unsubstituted or substituted. Especially preferred activated aromatic groups include, but are not intended to be limited to; phenyl, pyridyl, benzimidazolyl, naphthyl, benzofuranyl, indolyl, and the like, said groups being either unsubstituted or substituted with from one to five, preferably one or two, groups independently selected from halo, $C_1$–$C_6$ alkyl, $C_1$–$C_6$ haloalkyl, hydroxy, carboxy, acyl, $COOR^2$, $CONR^2R^3$, $CONH(C_1$–$C_6$ alkoxy), cyano, $C_1$–$C_6$ alkoxy, nitro, $NR^2R^3$, $NHCOR^2$, $SR^2$, $SO_2(NR^2R^3)$, $SO_2R^2$, and the like. Most preferred activated aromatic groups are 4-chlorophenyl, 3,4-dimethoxyphenyl, benzimidazolyl, or substituted benzimidazolyl. The leaving group defined as X is preferably halo, and more preferably bromide or iodide.

The reaction of Scheme 3 proceeds in the presence of a palladium catalyst. Preferred palladium catalysts include bis(dibenzylideneacetone)palladium (0) and bis(acetonitrile)palladium(II) chloride. Where the palladium catalyst is complexed to ligands, at least one of the ligands may be bound to an insoluble solid support if desired. The palladium catalyst may be present in from about 2 to about 25 mole percent based on the amount of substrate. The amount of palladium catalyst ranging from about 5 to about 10 mole percent is preferred, and about 5–7 mole percent is most preferred for the process of the present invention. It is also desirable that the palladium catalyst be freshly prepared prior to use. The palladium catalyst may alternatively be generated in situ from an appropriate source of palladium. This alternative is a further embodiment of the present invention.

The reaction of Scheme 3 is carried out in the presence of an amine base and a proton source. The amine base may be any primary, secondary, or tertiary amine that is sufficiently soluble in the reaction medium to affect the desired reaction. In certain circumstances it may be desirable to immobilize the amine base on a solid support. Such an amine is well known in the art. Preferable amine bases include, but are not intended to limited to; diethylamine, diisopropylamine, triethylamine, piperidine, pyridine, dimethylaminopyridine, and the like. Suitable proton sources include any organic or inorganic acid that is soluble in the reaction medium. In certain circumstances it may be desirable to immobilize the acid on a solid support. Such an acid is well known in the art. Preferable proton sources include, but are not intended to limited to; formic acid, acetic acid, benzoic acid, p-toluenesulfonic acid, methanesulfonic acid, and the like. In addition, an organosilane could be employed in combination with an organic or inorganic acid to serve as a proton source. Preferred organosilanes-include, but are not intended to be limited to, trialkylsilanes such as triethylsilane and the like.

Suitable reaction media useful for the process of the invention is one which is be capable of dissolving a sufficient amount of the substrate for the reaction to proceed. It is important to note that the selectivity of the reaction may be affected by the choice of solvent. For example, in some instances, toluene and acetone displayed the opposite regioselectivity. Organic solvents useful as reaction media for the process of this invention include, but are not intended to be limited to; ethers such as tetrahydrofuran, tetrahydropyran, dioxane, diethyl ether, diisopropyl ether, and the like; alkyl nitriles such as acetonitrile, propionitrile, and the like; and alkyl acetates such as methyl acetate, ethyl acetate, and the like. In addition, solvents such as dimethylformamide, methanol, ethanol, 2-butanone, toluene, benzene, acetone, and the like can be used. While all of these organic solvents are useful, certain solvents are preferred. Preferred organic solvents include but are not intended to limited to: tetrahydrofuran, acetonitrile, and ethylacetate. It is not necessary to rigorously exclude water from the process of the present invention.

The process may be carried out over a large range of concentrations depending upon the solubility of the propiolamide in the chosen reaction medium. The reaction may also be performed on slurries of the propiolamide, or neat, so long as a sufficient amount of the propiolamide is soluble in the reaction medium for the reaction to proceed. Preferably the process is performed at a concentration from about 0.005 molar to about 1 molar. A concentration of about 0.01 molar to about 0.03 molar is most preferred.

Reactions employing the process of the invention are preferably performed at the reflux temperature of the chosen reaction medium. The reactions may be performed at temperatures below reflux if convenient or desired. The skilled artisan will appreciate that reaction rates typically decrease as temperature is lowered. The overall reaction rate enhancement due to the process of the invention, however, renders lower temperature reactions synthetically useful in many cases. In general, the reaction is substantially complete after about 1 to about 36 hours when conducted at a temperature in the range of from about 10° C. to about 150° C. The reaction is preferably conducted at a temperature in the range of from about 20° C. to about 80° C. for about 3 to about 8 hours.

The process of the invention is performed by combining the substrates with a proton source, a palladium catalyst, and an amine base in a suitable reaction medium. Once the reaction is complete as measured by consumption of the propiolamide, the resultant product is isolated by standard extractions and filtrations. If desired, the product may be further purified by chromatography, crystallization or distillation as appropriate.

The order and manner of combining the reactants are not important and may be varied as a matter of convenience. For example, the substrates, proton source, palladium catalyst, and amine base may first be combined and then the reaction medium added. Alternatively, the substrates may first be dissolved in an appropriate reaction medium and this solution added to a mixture of the proton source, palladium catalyst, and amine base. Also, a solution of the substrates in an appropriate reaction medium may be added to a slurry of the proton source, palladium catalyst and amine base in the same reaction medium. Furthermore, a first slurry containing part of the substrates in an appropriate reaction medium may be added to a second slurry of the remaining reactants in an appropriate reaction medium as is desired or convenient. All of these methods are useful for the process of the present invention. Preferably the proton source is added as the final reagent or is added simultaneously with the propiolamide to a solution of the activated aromatic group, an amine base, and a palladium catalyst.

Although the stoichiometry of the reaction is not crucial, the process of the present invention is generally carried out with 1 equivalent of propiolamide, 1 to about 3 equivalents of Ar-X, 1 to about 5 equivalents of an amine base, and 1 to about 4 equivalents of a proton source. Preferably the stoichiometry is; 1 equivalent of propiolamide, 1 equivalent of Ar-X, 2–4 equivalents of an amine base, and 1–3 equivalents of a proton source.

The degree of regioselectivity achieved by the methodology presented herein varies depending on the conditions under which the reaction is performed. Scheme 4 below and the following tables illustrate this observation. Scheme 4 describes the hydroarylation reaction of 1-isopropylsulfonly-2-amino-6-iodobenzimidazole with 3-fluorophenylpropiolamide.

TABLE 2

Various catalysts for hydroarylation in ethyl acetate (Scheme 4)

| Catalyst | Time (h) | % β-isomer[b] | % α-isomer[b] | Isomer ratio β/α |
|---|---|---|---|---|
| Pd(ACN)$_2$Cl$_2$ | 2 | 47 | 11 | 4.4:1 |
| Pd(dba)$_2$ | 1 | 55 | 15 | 3.7:1 |
| Pd(OAc)$_2$ | 1.5 | 43 | 18 | 2.4:1 |
| PdCl$_2$ | 2 | 50 | 19 | 2.6:1 |
| Pd(TFA)$_2$ | 3 | 44 | 22 | 2:1 |
| Pd(BnCN)$_2$Cl$_2$ | 1 | 36 | 15 | 2.5:1 |
| Pd(PPh$_3$)$_2$(OAc)$_2$ | 1 | 20 | 9 | 2.2:1 |

[a]Reactions run using 6–7% catalyst, 3.3 equiv. piperidine, 2.6 equiv. formic acid in ethyl acetate at reflux.
[b]Reverse-phase HPLC area percents.

Scheme 4

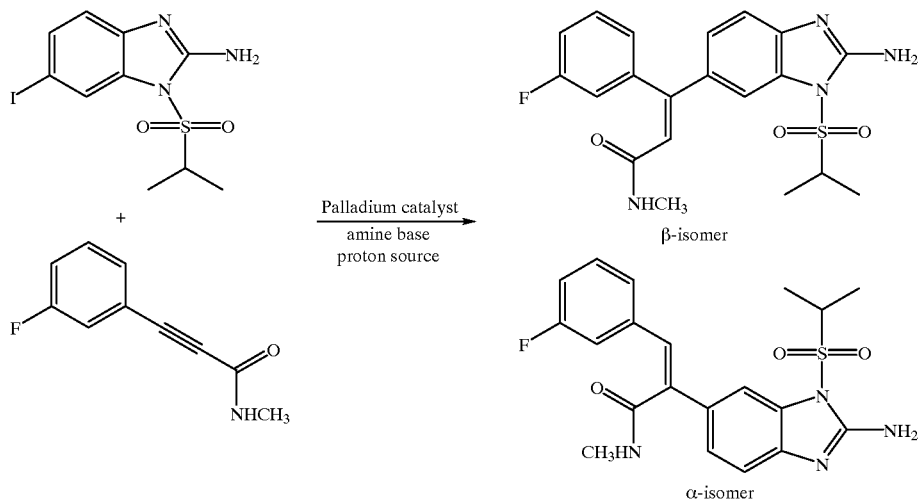

Table 1 describes the wide variety of solvents in which the hydroarylation reaction of Scheme 4 shows regioselectivity.

TABLE 1

Various solvents for hydroarylation (Scheme 4)

| Solvent | Temp. | °C. Time (h) | % β-isomer[b] | % α-isomer[b] | Isomer ratio β/α |
|---|---|---|---|---|---|
| DMF | 50–55 | 52 | 31 | 27 | 1.1:1 |
| EtOAc | reflux | 2 | 47 | 11 | 4.4:1 |
| ACN | reflux | 2 | 41 | 16 | 2.6:1 |
| MeOH | reflux | 24 | 30 | 27 | 1.1:1 |
| 2-butanone | 60 | 1.5 | 19 | 8 | 2:1 |
| i-PrOAc | 60–65 | 3 | 29 | 28 | 1.4:1 |

[a]Reactions run using 6–7% Pd(ACN)$_2$Cl$_2$, 3.3 equiv. piperidine, 2.6 equiv. formic acid.
[b]Reverse-phase HPLC area percents.

Table 2 illustrates that regioselectivity can be achieved by utilizing a variety of different catalysts and therefore the methodology described herein is generally applicable to both Pd(0) and Pd(II) catalysts.

Another parameter that contributes to the regioselectivity of the reaction is the concentration of the various substrates. The present inventors discovered that performing the hydroarylation reactions at a much more dilute concentration (about 0.02 mmol of reagents/1 ml solvent) dramatically improved the isomer ratios. For example, the hydroarylation in refluxing ethyl acetate with bis (dibenzylideneacetone)palladium(0) at 0.02M gave an isomer ratio of 17:1 as compared to a ratio of approximately 4:1 in more concentrated conditions. Reactions run more dilute than this showed no further improvements.

Table 3 illustrates the effect of concentration on regiochemical outcome of the reaction in different solvents.

TABLE 3

Various solvents at 0.02M (Scheme 4)[a]

| Solvent | Temp. | Isomer ratio[b] β/α |
|---|---|---|
| EtOAc | reflux | 17:1 |
| THF | reflux | 20:1 |
| CHCl$_3$ | reflux | 5.8:1 |

TABLE 3-continued

Various solvents at 0.02M (Scheme 4)[a]

| Solvent | Temp. | Isomer ratio[b] β/α |
|---------|-------|---------------------|
| MeOH | reflux | 3.5:1 |
| DMF | 60° C. | 2:1 |

[a]Reactions run using 6–7% Pd(dba)$_2$, 3.3 equiv. piperidine, 2.6 equiv. formic acid.
[b]Reverse-phase HPLC area percents.

Assay System

The reactions were assayed by HPLC using a Zorbax SB-C$_8$ column (4.6 mm×25 cm). Peaks were detected with a UV detector at 230–254 nm. The assays were performed at a flow rate of 1 mL/min. The solvent systems were 1:1 acetonitrile and 0.01N H$_2$SO$_4$ in water.

SYNTHETIC SCHEMES

Substituted propiolamides, of the formula (A), can be prepared by methods known in the art and through utilization of the scheme illustrated below.

Scheme 5

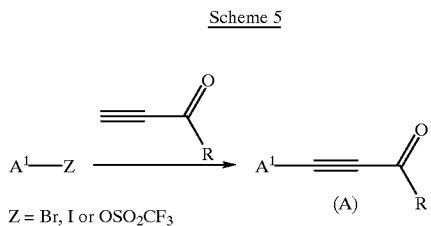

Z = Br, I or OSO$_2$CF$_3$

An appropriately substituted aromatic triflate or aromatic iodide can be coupled with a propiolamide to yield compounds of the formula (A). The coupling is accomplished in the presence of a solvent, an amine base, a palladium catalyst, and copper iodide. Solvent choice is not critical so long as the solvent employed is inert to the ongoing reaction and the reactants are sufficiently solubilized to effect the desired reaction. An especially preferred solvent is ethylacetate and dimethylsulfoxide. While the reaction can be accelerated through elevation of temperature, in general, it is substantially complete after about 3 to about 36 hours when conducted at ambient temperature. Suitable amines include, but are not intended to be limited to; diethylamine, diisopropylamine, triethylamine, piperidine, pyridine, dimethylaminopyridine, and the like. Preferred bases are diisopropylamine and triethylamine. Preferred palladium catalysts are bis(triphenylphosphine)palladium(II) acetate, and bis(triphenylphosphine)palladium(II) chloride. The skilled artisan will appreciate that while palladium catalysts are usually utilized in an amount equal to 5 mole-percent of the amount of reactants to be coupled it may be desirable to utilize significantly greater or lesser quantities depending upon the characteristics of the particular coupling reaction to be affected. Copper iodide is utilized in an amount equal to 20 mole-percent of the amount of reactants to be coupled. A skilled artisan will appreciate that the amount of copper iodide required may also vary significantly depending upon the characteristics of the reaction being catalyzed.

Appropriately substituted aromatic halides are generally commercially available or may be prepared by methods well know in the art. Substituted aromatic triflates are prepared from the corresponding commercially available aromatic hydroxy compounds by methods well known in the art. See Stang, et al., *Synthesis*, 58–126 (1982).

Compounds of formula A–X are well known by skilled artisans and are commercially available or can be prepared from commercially available starting materials by techniques well known in the art. By way of example, compounds of formula (B) can be prepared from commercially available benzimidazole according to the scheme illustrated below.

Scheme 6

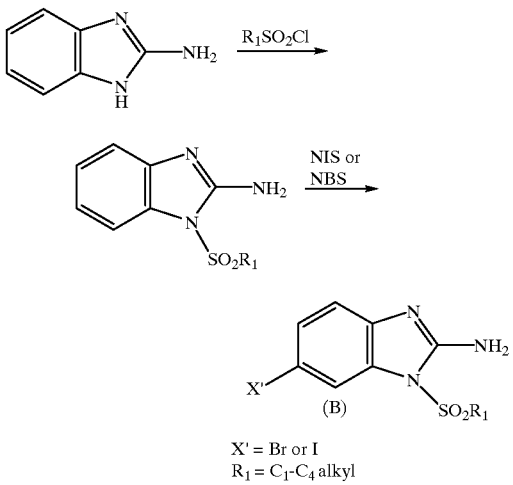

X' = Br or I
R$_1$ = C$_1$-C$_4$ alkyl

Benzimidazole can be sulphonated by an alkylsulphonyl chloride. The sulphonation is typically carried out by slowly adding the alkylsulphonyl chloride to a solution of benzimidazole in the presence of a base. Suitable bases include: sodium hydroxide, sodium bicarbonate, sodium carbonate, diethylamine, diisopropylamine, triethylamine, piperidine, pyridine, dimethylaminopyridine, and the like. Preferred bases are sodium hydroxide and triethylamine. Solvent choice is not critical so long as the solvent employed is inert to the ongoing reaction and the reactants are sufficiently solubilized to effect the desired reaction. Preferred solvents include water/acetonitrile and methylene chloride. In general, the reaction is substantially complete after about 1 to about 24 hours when conducted at a temperature in the range of from about 0° C. to about 40° C. The reaction is preferably conducted at a temperature in the range of from about 10° C. to about 30° C. for about 3 to 8 hours.

The sulphonated benzimidazole can then be halogenated with n-iodosuccinamide or n-bromosuccinamide in an appropriate solvent. An especially preferred solvent is acetic acid. In general, the reaction is substantially complete after about 1 to 24 hours when conducted at a temperature in the range of from about 20° C. to about 120° C. The reaction is preferably conducted at a temperature in the range of from about 30° C. to about 80° C. for about 3 to 8 hours.

PREPARATIONS AND EXAMPLES

The following examples and preparations are provided merely to further illustrate the invention. The scope of the invention is not to be construed as merely consisting of the following examples. In the following examples and preparations, melting point, nuclear magnetic resonance spectra, mass spectra, high pressure liquid chromatography over silica gel, gas chromatography, N,N-dimethylformamide, palladium on charcoal, tetrahydrofuran, ethyl acetate, thin layer chromatography and elemental analysis may be abbreviated mp, NMR, MS, HPLC, GC, DMF, Pd/C, THF, EtOAc, TLC and EA respectively. The terms "mp", "EA", "TLC", "NMR", and "MS", when being utilized in the preparations, indicate that the data indicated was consistent with the desired structure.

PREPARATIONS

Preparation 1

Propiolamide

Aqueous ammonia (29% in water, 14.0 mL) in an equal volume of methanol, was cooled to −78° C. for the dropwise addition of methyl propiolate (4.2 g, 0.0502 mmol) over 15 min. via an addition funnel. The mixture was stirred for 1 h. at −78° C. before warming to room temperature. The solvent was removed at 25° C. under vacuum to obtain 3.04 g product (87.7% yield). mp 60.5–62° C.

Preparation 2

N-methyl propiolamide

Methylamine (40% in water, 22.0 mL) in an equal volume of methanol was cooled to −78° C. in a 250 mL r.b. flask for the dropwise addition of methyl propiolate (20.0 g, 0.238 mol) over 15 min. via an addition funnel. The mixture was stirred for 3 h. at −78° C. before warming to room temperature. The solvent was removed at 25° C. under vacuum. The resulting solid was slurried in methanol and reconcentrated two times to remove any water. The slightly yellow solid was slurried in diethyl ether and cooled to −30° C. before filtering to obtain 18.74 g of a white crystalline solid (95.0% yield). mp 88° C. (lit. mp 90–91° C.)

Preparation 3

N,N-dimethyl propiolamide

Dimethylamine (40% in water, 26.7 g, 0.237 mol) in 50.0 mL methanol was cooled to −78° C. for the dropwise addition of methyl propiolate (20.0 g, 0.238 mol) over 1 hour. The mixture was kept at −78° C. for 4 h. before allowing to warm to room temperature. This mixture was stirred at room temperature for 1 h. before the solvent was removed under vacuum at room temperature to obtain a viscous yellow-orange liquid. This liquid was cooled to −10° C. to form a solid. This solid was slurried in diethyl ether and cooled to −30° C. to obtain 14.97 g of a yellow solid in two lots (65% yield). $^1$H NMR shows N,N-dimethyl propiolamide and the 1,4-addition product. This material was recrystallized from cold methanol to obtain clean product. mp 65–67° C.

General Procedure A: Coupling To Propiolamides

Preparation 4

N-methyl-3-(1-naphthyl)propiolamide

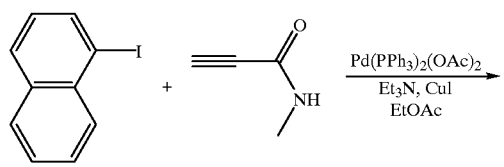

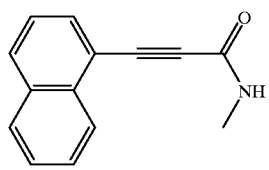

1-Iodonaphthalene (10.39 g, 40.91 mmol), N-methyl propiolamide (4.39 g, 52.87 mmol), bis(triphenylphosphine) palladium(II) acetate (2.45 g, 3.27 mmol), copper iodide (1.55 g, 8.15 mmol) and triethylamine (17.1 mL, 122.67 mmol) were stirred in 200 mL ethyl acetate at room temperature. After 1 hour, N-methyl propiolamide (7.1379 g, 85.9 mmol) was added in portions, along with 75 mL H$_2$O to dissolve the tar that had formed in the flask. After another hour additional water was added and the mixture was separated into the two layers. The organic layer was washed with water, brine, dried over MgSO$_4$, and concentrated under vacuum at room temperature to a solid, which was reslurried in ethylacetate to provide product in 95.1% yield. mp 114–116° C. MS General Procedure B: Coupling To Propiolamides Preparation 5

N-methyl-3-(9-phenanthryl)propiolamide

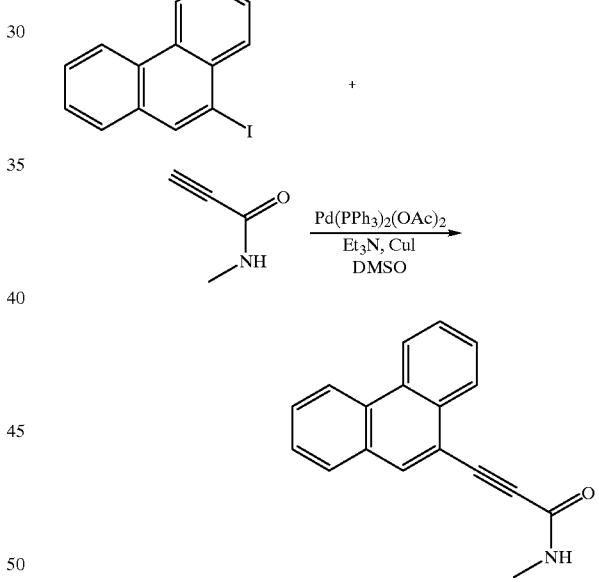

9-Iodophenanthrene (5.93 g, 19.49 mmol), N-methyl propiolamide (1.96 g, 23.56 mmol), bis(triphenylphosphine) palladium(II) acetate (1.15 g, 1.54 mmol), copper iodide (0.743 g, 3.90 mmol), and triethylamine (6.0 mL, 43.05 mmol), were stirred at room temperature in 130 mL DMSO overnight. The mixture was diluted with water and extracted 2× with ethyl acetate. The organics were washed 2× with water, once with brine, dried over MgSO$_4$ and concentrated to 6.98 g of a tan solid. This solid was reslurried in toluene and filtered to give 4.13 g (82% yield) of product in 4 crops. mp 140–142° C. MS Preparation 6

3-(3-fluorophenyl)-N-methylpropiolamide

According to preparation 4, 3-flouroiodobenzene (20.0 g) was reacted and 16.70 g crude product was obtained from the reaction. Reslurrying in cold toluene gave two crops of clean product (13.09 g, 82.0% yield). mp 91–93° C. MS Preparation 7

3-(4-anisyl)-N-methylpropiolamide

According to preparation 4, 4-iodoanisole (13.5 g) was reacted and 8.34 g of product was formed as a white solid in 76% yield. mp 123–124° C. MS Preparation 8

3-(4-α,α,α-trifluoromethylphenyl)-N-methylpropiolamide

According to preparation 4, 4-α,α,α-triflouromethyliodobenzene (1.2 g) was reacted and, 0.73 g of product was obtained as a white crystalline solid in 85% yield. mp 160–162° C. MS Preparation 9

N-methyl-3-(2-tolyl)propiolamide

According to preparation 5, 2-iodotoluene (1 g) was reacted and 0.76 g of product was obtained as a white solid in 95% yield. mp 52–55° C. MS Preparation 10

N-methyl-3-(4-carbomethoxyphenyl)propiolamide

According to preparation 4, methyl-4-iodobenzoate (7.27 g) was reacted and 4.78 g of an off-white solid was obtained (79% yield). MS, Analysis.

Preparation 11

3-(2-chloro-5-α,α,α-trifluoromethylphenyl)-N-methylpropiolamide

According to preparation 5, 2-chloro-5-triflouromethyliodobenzene (20 g) was reacted and 17 g of product obtained, a 95% yield. mp 129° C. MS Preparation 12

3-(3-chloro-4-methylphenyl)-N-methylpropiolamide

According to preparation 5, 3-chloro-4-methyliodobenzene (1.2 g) was reacted and 0.9 g of product was obtained. MS, Analysis.

Preparation 13

N-methyl-3-[4-(1-pyrrole)-phenyl]propiolamide

According to preparation 5, 1-(4-iodophenyl)pyrrole (6.3 g) was reacted and 3.41 g of product was obtained in 64% yield. MS, Anal.

Preparation 14

3-(4-α,α,α-trifluoromethylphenyl)propiolamide

According to preparation 4, 4-trifluoromethyliodobenzene (2.9 g) was reacted and, 2.13 g of product was obtained as a white crystalline solid in 92% yield. MS, Analysis.

Preparation 15

N-(2-phenethyl)-3-phenylpropiolamide

Phenethylamine (0.908 g, 7.5 mmol) was combined with phenylpropiolic acid (1.0 g, 6.8 mmol), EDCI (7.5 mmol), and diisopropylethylamine (7.5 mmol) in 30 ml of methylene chloride. The reaction was allowed to stir at room temperature overnight. The organic portion was washed with dilute HCl and brine and then dried over magnesium sulfate. The solvent was removed in vacuo and the residue recrystallized from diethylether to provide 1.3 g (76%) of product. NMR.

Preparation 16

(S)-N-(Methylphenylglycinate)phenylpropiolamide

According to preparation 15, (S)-(+)-phenylglycine methyl ester hydrochloride (1.5 g, 7.5 mmol) was reacted with phenylpropiolic acid (1.0 g, 6.8 mmol) to provide 2.0 g (91%) of product. NMR.

Preparation 17

N-phenyl-3-phenylpropiolamide

According to preparation 15, aniline (0.700 g, 7.5 mmol) was coupled to phenylpropiolic acid (1.0 g, 6.8 mmol) to provide 1.2 g (73%) of product. NMR.

Preparation 18

Pyrrolyl-3-phenylpropiolamide

According to preparation 15, pyrrolidine (2.43 g, 34 mmol) was coupled to phenylpropiolic acid (5.0 g, 34.2 mmol) to provide 5.1 g (75%) of product. NMR.

Preparation 19

Morpholino-2-thienylpropiolamide

According to preparation 4, Morpholinopropiolamide (1.6 g, 11.4 mmol) was reacted with 2-iodothiophene (2.0 g, 9.5 mmol) to provide 0.370 g (17.6%) of product. NMR.

Preparation 20

Morpholino-(9-phenanthracyl)propiolamide

According to preparation 4, Morphilinopropiolamide (3.8 g, 27.6 mmol) was reacted with 9-iodophenanthrene (7.0 g, 23.0 mmol) to provide 5.8 g (79%) of prodict. NMR.

Preparation 21

3-(2-Thienyl)propiolamide

According to preparation 4, propiolamide (1.68 g, 24.45 mmol) was coupled with 2-iodothiophene (3.2 g, 15.67 mmol) to provide 1.29 g (55%) of product. NMR.

Hydroarylation of Aryl Propiolamides

EXAMPLE 1

(E)-3-(4-anisyl)-3-(3-fluorophenyl)-N-methyl-2-propenamide

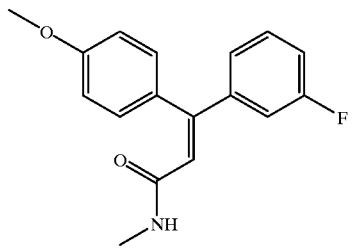

3-(4-anisyl)-N-methylpropiolamide 0.5 g (2.6 mmol), 3-fluoroiodobenzene (1 equiv.), and bis(dibenzylideneacetone)palladium(0) (7 mol%) were dissolved in ethyl acetate (0.02 mmol propiolamide/L solvent). Diethylamine (3.3 equiv.) was added, followed by formic acid (2.6 equiv.), and the solution was heated to reflux until reaction completion (2–18 h.). The reaction was then cooled to room temperature and washed with dilute HCl, then dilute NaOH, and finally brine. The organics were dried over anhydrous magnesium sulfate, and the solvent was removed under vacuum. Product was isolated from the crude mixture either by flash column chromatography (3% MeOH/CHCl$_3$; silica) or crystallization (1:1 EtOAc/Et$_2$O). The product (0.631 g) was isolated in 85% yield as a white solid. mp 118–122° C. MS (FD$^+$) Calcd. for C$_{17}$H$_{16}$NO$_2$F: 285.32; found: 285.1 (M$^+$ 100%).

EXAMPLE 2

(Z)-3-(4-anisyl)-3-(3-fluorophenyl)-N-methyl-2-propenamide

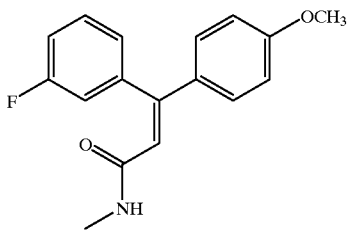

According to the procedure in example 1, (3-fluorophenyl)-N-methylpropiolamide (1 g) and 4-iodoanisole were reacted to give product (1.3 g) in 80% yield. mp 165–168° C.; MS (FD$^+$) Calcd. for C$_{17}$H$_{16}$NO$_2$F: 285.32; found: 285.1 (M$^+$ 100%).

EXAMPLE 3

(Z)-N-methyl-3-(1-naphthyl)-3-(9-phenanthryl)-2-propenamide

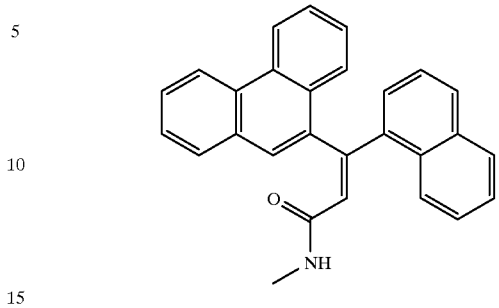

According to the procedure in example 1, 9-phenanthryl-N-methylpropiolamide (1 g) and 4-iodonaphthalene were reacted to give product (1.2 g) in 79% yield. mp 135° C. MS (FD$^+$) Calcd. for C$_{28}$H$_{21}$NO: 387.49; found: 387.2 (M$^+$ 100%).

EXAMPLE 4

(E)-3-(4-α,α,α-trifluoromethylphenyl)-3-(3-fluorophenyl)-N-methyl-2-propenamide

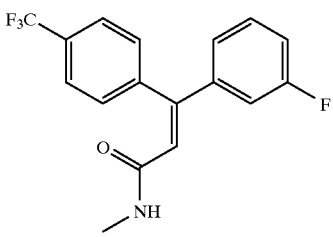

According to the procedure in example 1, (4-trifluoromethylphenyl)-N-methylpropiolamide (1 g) and 3-fluoroiodobenzene were reacted to give product (0.9 g) in 64% yield. MS (FD$^+$) Calcd. for C$_{17}$H$_{13}$NOF$_4$: 323.29; found: 323.4 (M$^+$ 100%). Anal. Calcd. for C$_{17}$H$_{13}$NOF$_4$: C, 63.16; H, 4.05; N, 4.33; F, 23.52. Found: 62.86; H, 4.04; N, 4.45; F, 23.71.

EXAMPLE 5

(Z)-3-(4-α,α,α-trifluoromethylphenyl)-3-(3-fluorophenyl)-N-methyl-2-propenamide

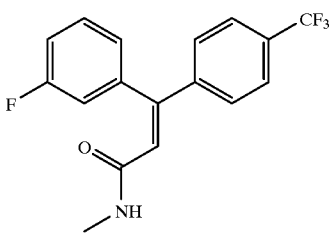

According to the procedure in example 1, (3-fluorophenyl)-N-methylpropiolamide (1 g) and 4-triflouromethyliodobenzene were reacted to give product (1.36 g) in 75% yield. mp 122–125° C.; MS (FD$^+$) Calcd. for C$_{17}$H$_{13}$NOF$_4$: 323.29; found: 323 (M$^+$ 100%).

EXAMPLE 6

(E)-N-(2-phenethyl)-3-(1-naphthyl)-3-phenylpropenamide

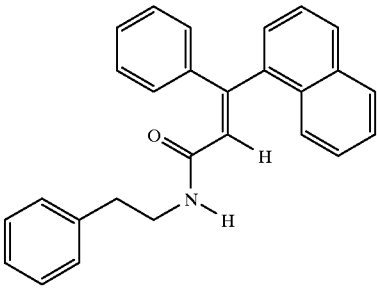

According to the procedure in example 1, (N-phenethyl)-phenylpropiolamide (0.394 mg, 1.58 mmol) was reacted with 1-iodonaphthalene (0.402 mg, 1.58 mmol) to provide 856 mg of crude product. Calculate $M^+$=377.4; Found: $M^+1$=378.1.

EXAMPLE 7

(E)-3-(4-anisyl)-3-(α,α,α-trifluoromethylphenyl)-N-methyl-2-propenamide

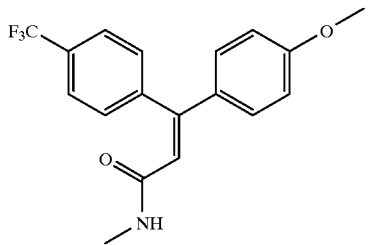

According to the procedure in example 1, (4-trifluoromethylphenyl)-N-methylpropiolamide (0.8 g) and 4-iodoanisole were reacted to give product (0.259 g) in 22% yield. MS (FD$^+$) Calcd. for $C_{18}H_{16}NO_2F_3$: 335.53; found: 335.14 ($M^+$ 100%). Anal. Calcd. for $C_{18}H_{16}NO_2F_3$: C, 64.47; H, 4.81; N, 4.18; F, 16.99. Found: C, 64.33; H, 4.85; N, 4.23.

EXAMPLE 8

(Z)-3-(4-anisyl)-3-(α,α,α-trifluoromethylphenyl)-N-methyl-2-propenamide

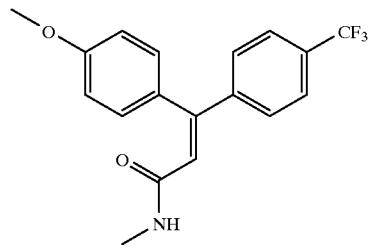

According to the procedure in example 1, (4-anisyl)-N-methylpropiolamide (0.635 g) and 4-α,α,α-triflouromethyliodobenzene were reacted to give product (0.563 g) in 50% yield. MS (FD$^+$) Calcd. for $C_{18}H_{16}NO_2F_3$: 335.53; found: 335.1 ($M^+$ 100%). Anal. Calcd. for $C_{18}H_{16}NO_2F_3$: C, 64.47; H, 4.81; N, 4.18; F, 16.99. Found: C, 64.35; H, 4.79; N, 4.19; F, 17.22.

EXAMPLE 9

(E)-3-(4-anisyl)-N-methyl-3-(2-tolyl)-2-propenamide

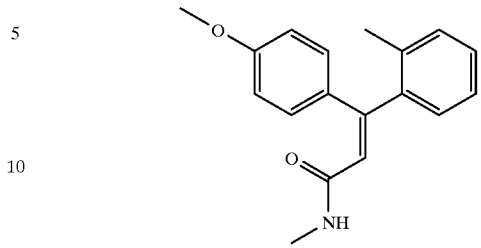

According to the procedure in example 1, (4-anisyl)-N-methylpropiolamide (0.5 g) and 2-iodotoluene were reacted to give product (0.61 g) in 82% yield. MS (FD$^+$) Calcd. for $C_{18}H_{19}NO_2$: 281.36; found: 281.2 ($M^+$ 100%). Anal. Calcd for $C_{18}H_{19}NO_2$: C, 76.84; H, 6.81; N, 4.98. Found: C, 76.61; H, 6.79; N, 5.20.

EXAMPLE 10

(Z)-3-(4-anisyl)-N-methyl-3-(2-tolyl)-2-propenamide

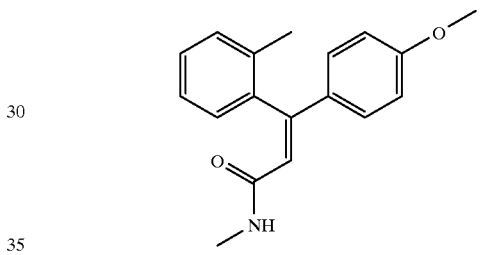

According to the procedure in example 1, (2-tolyl)-N-methylpropiolamide (0.5 g) and 4-iodoanisole were reacted to give product (0.72 g) in 88% yield. MS (FD$^+$) Calcd for $C_{18}H_{19}NO_2$: 281.36; found: 281.1 ($M^+$ 100%). Anal. Calcd. for $C_{18}H_{19}NO_2$: C, 76.84; H, 6.81; N, 4.98. Found: C, 76.60; H, 6.84; N, 5.08.

EXAMPLE 11

(Z)-3-(4-α,α,α-trifluoromethylphenyl)-N-methyl-3-(2-tolyl)-2-propenamide

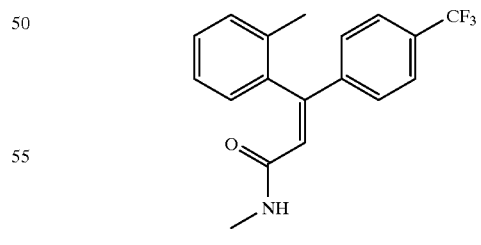

According to the procedure in example 1, (2-tolyl)-N-methylpropiolamide (0.5 g) and 4-α,α,α-trifluoromethyliodobenzene were reacted to give product (0.79 g) in 85% yield. MS (FD$^+$) Calcd for $C_{18}H_{16}NOF_3$: 319.33; found: 319.1 ($M^+$ 100%). Anal. Calcd. for $C_{18}H_{16}NOF_3$: C, 67.71; H, 5.05; N, 4.39. Found: C, 67.54; H, 5.13; N, 4.36.

EXAMPLE 12

(E)-3-(3-fluorophenyl)-N-methyl-3-(1-naphthyl)-2-propenamide

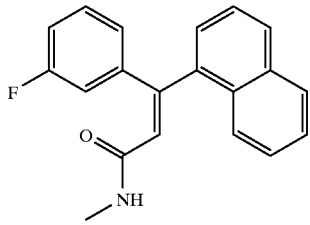

According to the procedure in example 1, (3-fluorophenyl)-N-methylpropiolamide (0.69 g) and 1-iodonaphthalene were reacted to give product (1.1 g) in 93% yield. mp 149–150° C. MS (FD$^+$) Calcd. for $C_{20}H_{16}NOF$: 305.37; found: 305.0 (M$^+$ 100%). Anal. Calcd. for $C_{20}H_{16}NOF$: C, 78.67; H, 5.28; N, 4.59; F, 6.22. Found: C, 78.40; H, 5.20; N, 4.70; F, 6.33.

EXAMPLE 13

(Z)-3-(3-fluorophenyl)-N-methyl-3-(1-naphthyl)-2-propenamide

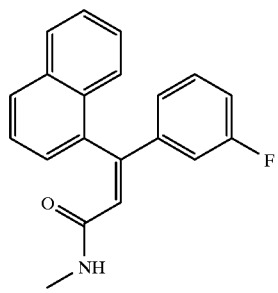

According to the procedure in example 1, (1-naphthyl)-N-methylpropiolamide (0.66 g) and 3-flouroiodobenzene were reacted to give product (0.69 g) in 72% yield. mp 152–153° C. MS (FD$^+$) Calcd. for $C_{20}H_{16}NOF$: 305.37; found: 305.1 (M$^+$ 100%). Anal. Calcd. for $C_{20}H_{16}NOF$: C, 78.67; H, 5.28; N, 4.59; F, 6.22. Found: C, 78.82; H, 5.27; N, 4.54; F, 6.38.

EXAMPLE 14

(E)-3-(4-anisyl)-N-methyl-3-(1-naphthyl)-2-propenamide

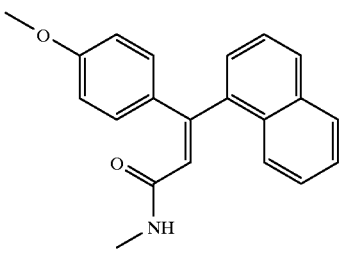

According to the procedure in example 1, (4-anisyl)-N-methylpropiolamide (0.50 g) and 1-iodonaphthalene were reacted to give product (0.60 g) 71% yield. mp 151–153° C. MS (FD$^+$) Calcd. for $C_{21}H_{19}NO_2$: 317.4; found: 317 (M$^+$ 100%). Anal. Calcd. for $C_{21}H_{19}NO_2$: C, 79.47; H, 6.03; N, 4.41. Found: C, 79.21; H, 6.05; N, 4.44.

EXAMPLE 15

(Z)-3-(4-anisyl)-N-methyl-3-(1-naphthyl)-2-propenamide

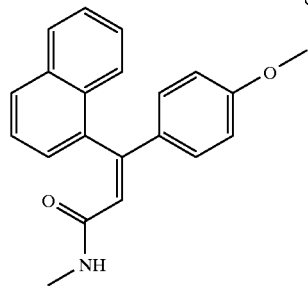

According to the procedure in example 1, (1-naphthyl)-N-methylpropiolamide (1.13 g) and 4-iodoanisole were reacted to give product (1.11 g) in 74% yield. mp 164–166° C. MS (FD$^+$) Calcd. for $C_{21}H_{19}NO_2$: 317.4; found: 317.0 (M$^+$ 100%). Anal. Calcd. for $C_{21}H_{19}NO_2$: C, 79.47; H, 6.03; N, 4.41. Found: C, 79.32; H, 6.05; N, 4.50.

EXAMPLE 16

(E)-3-(4-α,α,α-trifluoromethylphenyl)-N-methyl-3-(1-naphthyl)-2-proenamide

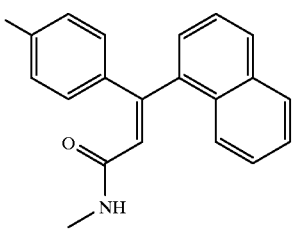

According to the procedure in example 1, (4-trifluoromethylphenyl)-N-methylpropiolamide (0.5 g) and 1-iodonaphthalene were reacted to give product (0.621 g) in 76% yield. mp 147–149° C. MS (FD$^+$) Calcd. for $C_{21}H_{16}NOF_3$: 355.37; found: 355.1 (M$^+$ 100%). Anal. calcd. for $C_{21}H_{16}NOF_3$: C, 70.98; H, 4.54; N, 3.94; F, 16.04. Found: C, 70.69; H, 4.74; N, 3.74; F, 15.97

EXAMPLE 17

(Z)-3-(4-α,α,α-trifluoromethylphenyl)-N-methyl-3-(1-naphthyl)-2-propenamide

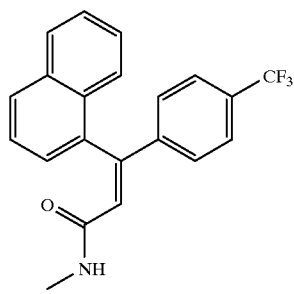

According to the procedure in example 1, (1-naphthyl)-N-methylpropiolamide (0.54g) and 4-α,α,α-trifluuromethyliodobenzene were reacted to give product (0.747 g) in 82% yield. MS (FD$^+$) Calcd. for $C_{21}H_{16}NOF_3$:

355.37; found: 355 (M⁺ 100%). Anal. Calcd. for C$_{21}$H$_{16}$NOF$_3$: C, 70.98; H, 4.54; N, 3.94; F, 16.04. Found: C, 71.10; H, 4.65; N, 3.98; F, 16.26.

EXAMPLE 18

(E)-N-methyl-3-(1-naphthyl)-3-(2-tolyl)-2-propenamide

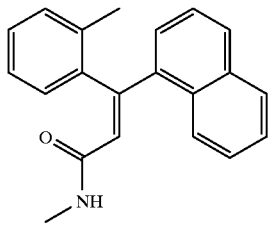

According to the procedure in example 1, (2-tolyl)-N-methylpropiolamide (1 g) and 1-iodonaphthalene were reacted to give product (1.46 g) in 84% yield. mp 185–187° C. MS (FD⁺) Calcd. for C$_{21}$H$_{19}$NO: 301.40; found: 301.0 (M⁺ 100%). Anal. Calcd. for C$_{21}$H$_{19}$NO: C, 83.69; H, 6.35; N, 4.65. Found: C, 83.59; H, 6.38; N, 4.86.

EXAMPLE 19

(Z)-N-methyl-3-(1-naphthyl)-3-(2-tolyl)-2-propenamide

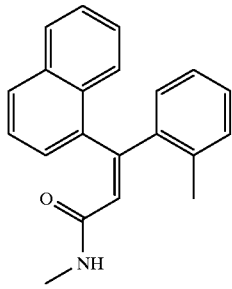

According to the procedure in example 1, (1-naphthyl)-N-methylpropiolamide (0.749 g) and 2-iodotoluene were reacted to give product (0.658 g) in 61% yield. mp 167–169° C. MS (FD⁺) Calcd. for C$_{21}$H$_{19}$NO: 301.40; found: 300.99 (M⁺ 100%). Anal. Calcd. for C$_{21}$H$_{19}$NO: C, 83.69; H, 6.35; N, 4.65. Found: C, 83.43; H, 6.62; N, 4.95.

EXAMPLE 20

(E)-3-(3-fluorophenyl)-N-methyl-3-(9-phenanthryl)-2-propenamide

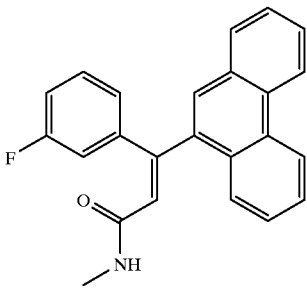

According to the procedure in example 1, (3-fluorophenyl)-N-methylpropiolamide (0.545 g) and 9-iodophenanthrene were reacted to give product (0.777 g) in 77% yield. mp 199–201° C. MS (FD⁺) Calcd. for C$_{24}$H$_{18}$NFO: 355.42; found: 355.1 (M⁺ 100%). Anal. Calcd. for C$_{24}$H$_{18}$NFO: C, 81.10; H, 5.11; N, 3.94; F, 5.35. Found: C, 81.12; H, 5.02; N, 3.91; F, 5.23.

EXAMPLE 21

(Z)-3-(3-fluorophenyl)-N-methyl-3-(9-phenanthryl)-2-propenamide

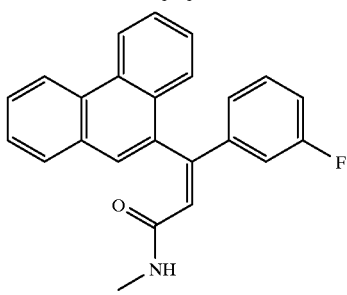

According to the procedure in example 1, (9-phenanthryl)-N-methylpropiolamide (1 g) and 3-flouroiodobenzene were reacted to give product (1.08 g) in 83% yield. mp 124° C. MS (FD⁺) Calcd. for C$_{24}$H$_{18}$NOF: 355.42; found: 355.18 (M⁺ 100%). Anal. Calcd. for C$_{24}$H$_{18}$NOF: C, 81.11; H, 5.10; N, 3.94. Found: C, 80.99; H, 5.17; N, 3.94.

EXAMPLE 22

(E)-3-(4-anisyl)-N-methyl-3-(9-phenanthryl)-2-propenamide

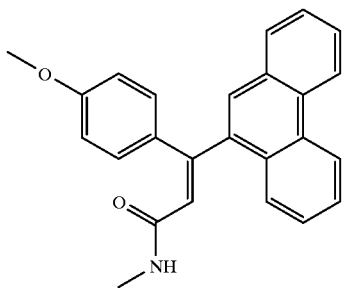

According to the procedure in example 1, (4-anisyl)-N-methylpropiolamide (0.975 g) and 9-iodophenanthrene were reacted to give product (1.32 g) in 72% yield. mp 156–158° C. MS (FD⁺) Calcd. for C$_{25}$H$_{21}$NO$_2$: 367.45; found: 367.0 (M⁺ 100%). Anal. Calcd. for C$_{25}$H$_{21}$NO$_2$: 81.72; H, 5.76; N, 3.81. Found: C, 81.81; H, 5.62; N, 3.94.

EXAMPLE 23

(Z)-3-(4-anisyl)-*N*-methyl-3-(9-phenanthryl)-2-propenamide

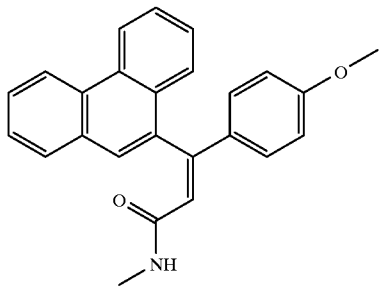

According to the procedure in example 1, (9-phenanthryl)-N-methylpropiolamide (1 g) and 4-iodoanisole were reacted to give product (1.2 g) in 83% yield. mp 176–179° C. MS (FD$^+$) Calcd. for $C_{25}H_{21}NO_2$: 367.45; found: 367.01 (M$^+$ 100%).

EXAMPLE 24

(E)-3-(4-α,α,α-trifluoromethyl)-*N*-methyl-3-(9-phenanthryl)-2-propenamide

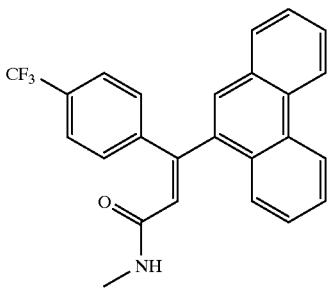

According to the procedure in example 1, (4-α,α,α-trifluoromethylphenyl)-N-methylpropiolamide (1 g) and 9-iodophenanthrene were reacted to give product (1.63 g) in 89% yield. mp 209–210° C. MS (FD$^+$) Calcd. for $C_{25}H_{18}F_3NO$: 405.42; found: 405.1 (M$^+$ 100%). Anal. Calcd. for $C_{25}H_{18}F_3NO$: C, 74.07; H, 4.48; N, 3.46; F, 14.06. Found: C, 74.21; H, 4.53; N, 3.59; F, 14.16.

EXAMPLE 25

(Z)-3-(4-α,α,α-trifluoromethylphenyl)-*N*-methyl-3-(9-phenanthryl)-2-propenamide

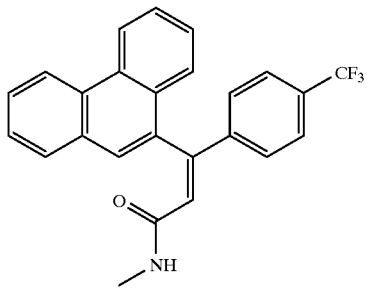

According to the procedure in example 1, (9-phenanthryl)-N-methylpropiolamide (1 g) and 4-α,α,α-trifluoromethyliodobenzene were reacted to give product (1.22 g) in 77% yield. mp 138–139° C. MS (FD$^+$) Calcd. for $C_{25}H_{18}F_3NO$: 405.42; found: 405.1 (M$^+$ 100%). Anal. Calcd. for $C_{25}H_{18}F_3NO$: C, 74.07; H, 4.48; N, 3.46; F, 14.06. Found: C, 73.98; H, 4.73; N, 3.72.

EXAMPLE 26

(E)-*N*-methyl-3-(9-phenanthryl)-3-(2-tolyl)-2-propenamide

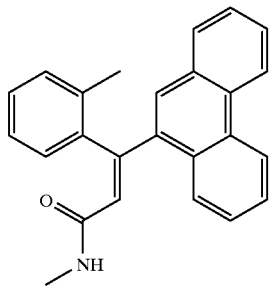

According to the procedure in example 1, (2-tolyl)-N-methylpropiolamide (0.76 g) and 9-iodophenanthrene were reacted to give product (1.38 g) in 90% yield. mp 247–248° C. MS (FD$^+$) Calcd. for $C_{25}H_{21}NO$: 351.47; found: 351.1 (M$^+$ 100%). Anal. Calcd. for $C_{25}H_{21}NO$: C, 85.44; H, 6.02; N, 3.99. Found: C, 84.16; H, 5.95; N, 4.21.

EXAMPLE 27

(Z)-*N*-methyl-3-(9-phenanthryl)-3-(2-tolyl)-2-propenamide

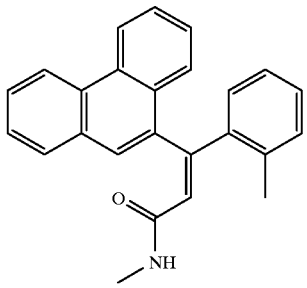

According to the procedure in example 1, (9-phenanthryl)-N-methylpropiolamide (1 g) and 2-iodotoluene were reacted to give product (0.85 g) in 62% yield. mp 144° C. IR (CHCl$_3$) 3450, 3011, 2219, 2205, 1652, 1521, 1494, 1452, 1415, 1265, 1242 cm$^{-1}$. MS (FD$^+$) Calcd. for $C_{25}H_{21}NO$: 351.47; found: 351.45

EXAMPLE 28

(E)-*N*-methyl-3-(1-naphthyl)-3-(9-phenanthryl)-2-propenamide

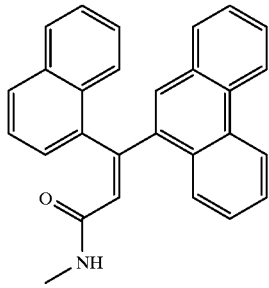

According to the procedure in example 1, (1-naphthyl)-N-methylpropiolamide (0.66 g) and 9-iodophenanthrene were reacted to give product (0.875 g) in 71% yield. mp 236–239° C. MS (FD$^+$) Calcd. for $C_{28}H_{21}NO$: 387.49; found: 387 (M$^+$ 100%). Anal. Calcd. for $C_{28}H_{21}NO$: C, 86.79; H, 5.46; N, 3.62. Found: C, 86.53; H, 5.49; N, 3.80.

EXAMPLE 29

(Z)-3-(3-fluorophenyl)-*N*-methyl-3-(2-tolyl)-2-propenamide

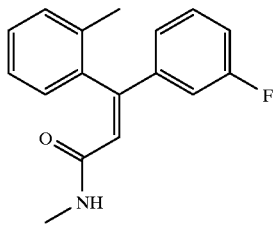

According to the procedure in example 1, (2-tolyl)-N-methylpropiolamide (0.9 g) and 3-flouroiodobenzene were reacted to give product (0.95 g) in 68% yield. MS (FD$^+$) Calcd. for $C_{17}H_{16}NOF$: 269.32; found: 269 (M$^+$ 100%). Anal. Calcd. for $C_{17}H_{16}NOF$: C, 75.82; H, 5.99; N, 5.20; F, 7.05. Found: C, 76.10; H, 6.00; N, 5.14; F, 6.98.

EXAMPLE 30

(Z)-N-methyl-3-(1-naphtyl)-3-[4-(1-pyrrolo)phenyl]-2-propenamide

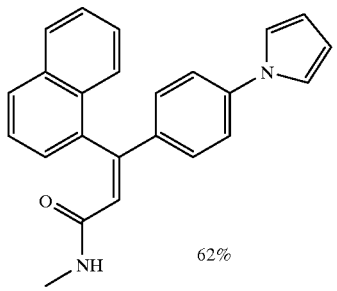

62%

According to the procedure in example 1, 1-(4-iodophenyl)pyrrole and (1-naphthyl)-N-methylpropiolamide were reacted to give product (0.603 g) in 62% yield. MS (FD$^+$) Calcd. for $C_{24}H_{20}N_2O$: 352.45; found: 352.0 (M$^+$ 100%). Anal. Calcd. for $C_{24}H_{20}N_2O$: C, 81.79; H, 5.72; N, 7.95. Found: C, 81.60; H, 5.56; N, 7.95.

EXAMPLE 31

(Z)-3-(4-anisyl)-*N*-methyl-3-[4-(1-pyrrolo)phenyl]-2-propenamide

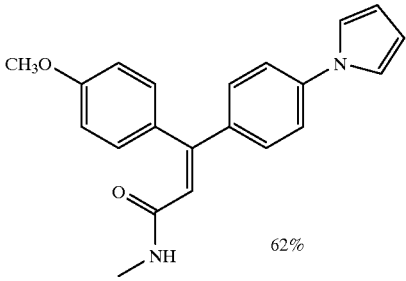

62%

According to the procedure in example 1, (4-anisyl)-N-methylpropiolamide and 1-(4-iodophenyl)pyrrole were reacted to give product (0.47 g) in 62% yield. mp 153–155° C. MS (FD$^+$) Calcd. for $C_{21}H_{20}N_2O_2$: 332.43; found: 332.17 (M$^+$ 100%).

EXAMPLE 32

(Z)-3-(3-fluorophenyl)-*N*-methyl-3-[4-(1-pyrrolo)phenyl]-2-propenamide

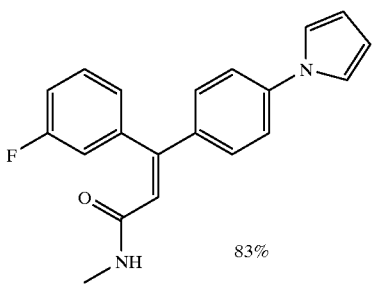

83%

According to the procedure in example 1, (3-fluorophenyl)-N-methylpropiolamide and 1-(4-iodophenyl)pyrrole were reacted to give product (0.594 g) in 83% yield. mp 147–149° C. MS (FD$^+$) Calcd. for $C_{20}H_{17}N_2OF$: 320.37; found: 320.1 (M$^+$ 100%).

EXAMPLE 33

(Z)-*N*-methyl-3-(2-tolyl)-3-[4-(1-pyrrolo)phenyl]-2-propenamide

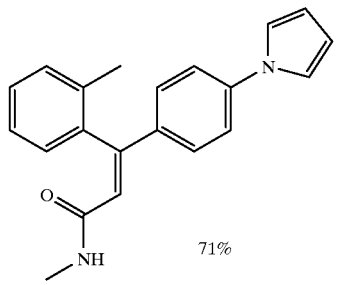

71%

According to the procedure in example 1, N-methyl-(2-tolyl)propiolamide and 1-(4-iodophenyl)pyrrole were reacted to give product (0.99 g) in 71% yield. mp 180–183° C. MS (FD$^+$) Calcd. for $C_{21}H_{20}N_2O$: 316.41; found: 316.1 (M$^+$ 100%).

EXAMPLE 34

(Z)-N-Morpholino-3-(9-phenanthracyl)-3-(3-flourophenyl)propenamide

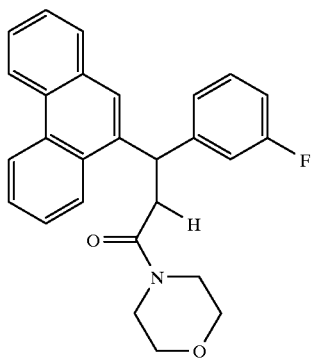

According to the procedure in example 1, N-morpholinophenanthrenyl propiolamide (0.46 g, 1.46 mol) was reacted with 3-fluoro-1-iodobenzene (0.17 mL, 1.45 mmol) to provide 0.48 g (46%) of the product. Calculate $M^+1 = 411.47$; Found: $M^+1=412.1$.

EXAMPLE 35

(E)-N-Methyl-3-(6-isatin)-3-(4-methoxy)propenamide

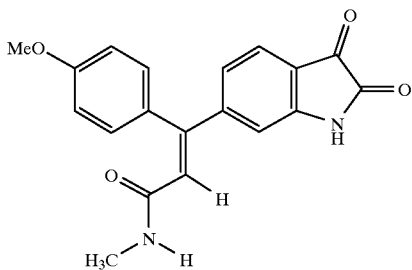

According to the procedure in example 1, N-methyl-4-anisylpropiolamide (517 g, 2.73 mmol) was reacted with 5-iodoisatin (0.742 g, 2.72 mmol) to provide 0.793 g (86%). Calculate $M^+=336.3$; Found: $M^+1=337$.

EXAMPLE 36

(E)-N-Methyl-1-naphthylpropenamide

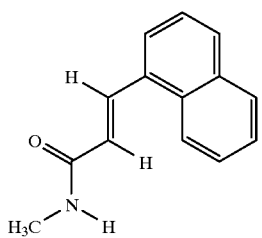

According to the procedure in example 1, iodonaphthalene (0.55 mL, 3.77 mmol) was reacted with N-methylpropiolamide (0.316 g, 3.80 mmol) to provide 0.986 g (123%) of the crude product. Calculate $M^+=211.2$; Found: $M^+1=212.1$.

EXAMPLE 37

(E)-N-Phenyl-3(1-naphyhyl)-3-phenylpropenamide

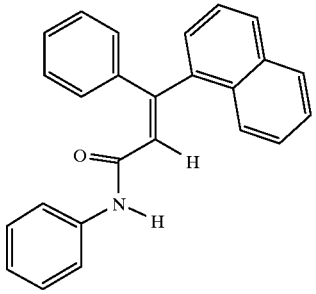

According to the procedure in example 1, phenyl-N-phenylpropiolamide (0.164 g, 0.741 mmol) was reacted with 1-iodonaphthalene (0.11 mL, 0.753 mmol) to provide 172 mg (40%) of product. Calculate $M^+=349.4$; Found: $M^+1=350$.

EXAMPLE 38

(E)-N-Pyrrolol-3-(1-naphyhyl)-3-phenylpropenamide

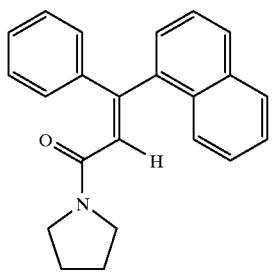

According to the procedure in example 1, (pyrrolidino) phenylpropiolamide (0.2079 g, 1.04 mmol) was reacted with 1-iodonaphthalene (0.15 mL, 1.03 mmol) to provide 0.366 g (59%) of product. Calculate $M^+=327.4$; Found: $M^+1=328$.

EXAMPLE 39

(Z)-N, O-Dimethylcarbamyl-3-(3-flourophenyl)-3-(4-triflouromethyl)propenamide

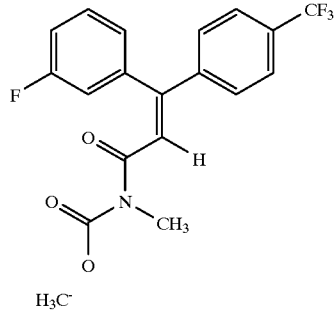

According to the procedure in example 1, (N-methyl)-N-methylcarbamiyl-3-fluorophenylpropiolamide (0.158 g, 0.670 inmol) was reacted with 4-iodobenzotrifluoride (0.187 g, 0.688 mmnol) to provide 0.219 g of crude product. Purified product was only 19% of the reaction product. Calculate $M^+=381.3$; Found: $M^+1=382$.

EXAMPLE 40

(E)-N-(Methylphenyl glycinate)-3-(5-pyrazolo)-3-phenylpropenamide

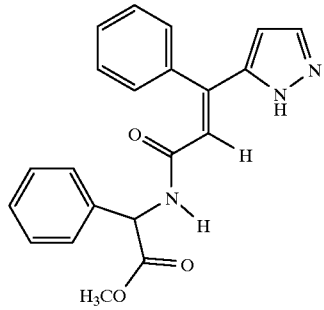

According to the procedure in example 1, (N-(S-methylphenylglycinate)phenylpropiolamide (0.469 g, 1.58 mmol) was reacted with 2-iodopyrazole (0.306 g, 158 mmol) to provide 396 mg (69%) of product. Calculate $M^+$=361.4; Found: $M^+1$=362.

EXAMPLE 41

(E)-N-(2-phenethyl)-3-phenyl-3-(2-thiophenyl)propenamide

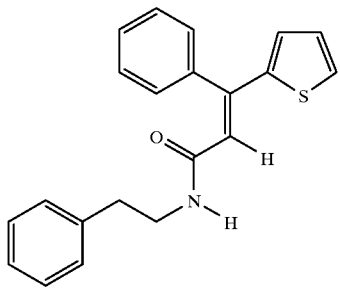

According to the procedure in example 1, (N-phenethyl)-phenylpropiolamide (0.394 mg, 1.58 mmol) was reacted with 2-iodothiophene (0.332 mg, 1.58 mmol) to provide 418 mg (52%) of product. Calculate $M^+$=333.5; Found: $M^+1$=334.

EXAMPLE 42

(E)-N-(methylphenylglycinate)-3-(1-naphthyl)-3-phenylpropenamide

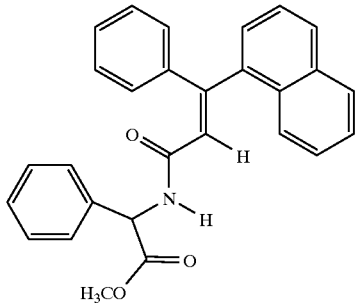

According to the procedure in example 1 (N-(S-)methylphenylglycinate)phenylpropiolamide (0.469 g, 1.58 mmol) was reacted with 1-iodonaphthalene (0.402 g, 158 mmol) to provide 1.1 g of crude product. Calculate $M^+$=421.4; Found: $M^+1$=422.

EXAMPLE 43

(E)-N-methyl-3-[6-(1-isopropylsulfonyl)-2-amino]benzimdazolyl-3-(3-flourophenyl)propenamide

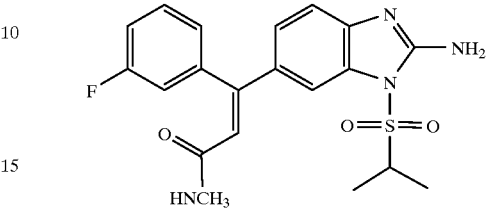

To a 2 L r.b. flask was added 7.94 g (0.0218 mol) of 1-isopropyl-2-amino-6-iodo-benzamidizole and 5.00 g (0.0282 mol) N-methyl-3-(3-fluorophenyl)propioamide in 750 mL ethyl acetate at room temperature. To this was added 0.40 g (0.0015 mol) bis(acetonitrile)palladium(II) chloride and 7.1 mL (0.0718 mol) piperidine, followed by 2.10 g (0.0557 mol) formic acid. This mixture was heated to reflux for 5 hours, adding 0.445 g more propioamide after 1 hour, before cooling to room temperature. About half of the solvent was removed under vacuum before water was added. The layers were separated, and the organics washed two times with water, once with brine, dried over $MgSO_4$ and concentrated to a semi-solid. 13.49 g of crude product (80.6% HPLC corrected yield) were obtained. This material was recrystallized in EtOAc to obtain 5.75 g product (60.0% yield). MS (FD$^+$): Calcd for $C_{20}H_{21}FN_4O_3S$: 416.47; found: 416.0 ($M^+$ 100%). Anal. Calcd. for $C_{20}H_{21}FN_4O_3S$: C, 57.68; H, 5.08; F, 4.56; N, 13.45; S, 7.70. Found: C, 58.29; H, 5.1; F, 4.69; N, 12.99; S, 7.15.

EXAMPLE 44

(E)-N-methyl-3-[6-(1-isopropylsulfonyl)-2-amino]benzimdazolyl-3-(2, 5-difluorophenyl)propenamide

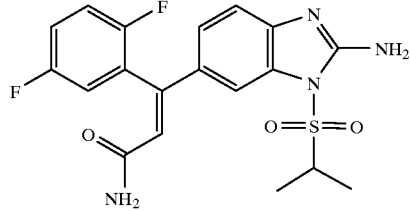

In a 2 L flask, 1-isopropyl-2-amino-6-iodo-benzamidazole (6.185 g, 0.0169 mol), bis(dibenzylideneacetone) palladium(0) (0.388 g, 0.000675 mol), and diethylamine (5.8 mL, 0.0561 mol) were dissolved in 750 mL ethyl acetate. Into an addition funnel was placed N-methyl-3-(2,5-difluorophenyl)propioamide (3.07 g, 0.0169 mol) in 60 mL ethyl acetate. Formic acid (1.5 mL, 0.0398 mol) was added all at once to the additon funnel. The contents of the 2 L flask were heated to reflux before the propioamide/formic acid solution was slowly added to the flask over several hours. The mixture was refluxed overnight. Additional propioamide (0.705 g) in 15 mL ethyl acetate was added, along with 0.09 mL formic acid to drive the reaction to completion. After refluxing overnight again, the mixture was cooled to room temperature, and half of the solvent was removed under vacuum. The remaining solution was washed with water, 1.0N NaOH, brine, dried (MgSO$_4$), and concentrated to 8.282 g of a yellow solid (53% HPLC-corrected yield). MS (FD$^+$): Calcd for C$_{19}$H$_{18}$N$_4$O$_3$F$_2$S: 420.437; found: 420.1 (M$^+$ 100%). Anal. Calcd. for C$_{19}$H18N$_4$O$_3$F$_2$S: C, 54.28; H, 4.32; N, 13.33; S, 7.63; F, 9.04. Found: C,54.02; H, 4.44; N, 13.18; S, 7.40; F, 9.31.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A process for preparing an acrylamide which comprises reacting a propiolamide with an activated aromatic ring system, wherein said activated ring system is activated with a leaving group selected from the group consisting of fluoro, chloro, bromo, and iodo, in the presence of a palladium catalyst, an amine base, and a proton source.

2. A process according to claim 1 wherein said leaving group is selected from the group consisting of bromo and iodo.

3. A process for preparing a compound of formula I

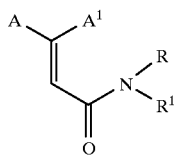

wherein A and A$^1$ are independently aryl, substituted aryl, heterocyclyl, or substituted heterocyclyl; and R and R$^1$ are independently hydrogen, C$_1$–C$_4$ alkyl, C$_1$–C$_4$ haloalkyl, phenyl, substituted phenyl, or R and R$^1$ combine together with the nitrogen atom to which they are attached to form a morpholinyl, piperidinyl, pyrrolidinyl, or piperazinyl ring; which comprises:

reacting a compound of formula II

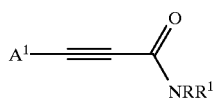

with a compound of formula III

   III wherein X is a leaving group selected from the group consisting of fluoro, chloro, bromo and iodo;

in the presence of a palladium catalyst, an amine base, and a proton source.

4. A process according to claim 3 wherein X is bromo or iodo.

5. A process according to claim 4 wherein R is NR$^1$R$^{1a}$, and R$^1$ and R$^{1a}$ a are independently hydrogen, C$_1$–C$_6$ alkyl, C$_1$–C$_4$ haloalkyl, substituted C$_1$–C$_6$ alkyl, C$_1$–C$_6$ alkoxy, (CH$_2$)$_n$ aryl, (CH$_2$)$_n$ substituted heterocyclyl, CO$_2$R$^4$, COR$^4$, CONR$^4$R$^5$, CHR$^5$CO$_2$R$^4$, CHR$^5$CONHR$^4$, or R$^1$ and R$^{1a}$ combine to form, together with the nitrogen to which they are attached, a morpholinyl, piperidinyl, pyrrolidinyl, or piperazinyl ring;

R$^4$ and R$^5$ are independently hydrogen, C$_1$–C$_6$ alkyl, substituted C$_1$–C$_6$ alkyl, C$_1$–C$_4$ haloalkyl, C$_1$–C$_6$ alkoxy, (CH$_2$)$_n$ aryl, (CH$_2$)$_n$ substituted aryl, (CH$_2$)n heterocyclyl, or (CH$_2$)$_n$ substituted heterocyclyl; and n is 0, 1, 2, 3, 4, 5, or 6.

6. A process according to claim 5 wherein n is 0, 1, 2, or 3.

7. A process according to claim 5 wherein R$^1$ and R$^{1a}$ combine to form, together with the nitrogen to which they are attached, a morpholinyl ring.

8. A process according to claim 5 wherein A and A$^1$ are independently clorophenyl or dimethoxyphenyl.

* * * * *